United States Patent
Hehner et al.

(12)
(10) Patent No.: US 6,685,926 B2
(45) Date of Patent: Feb. 3, 2004

(54) METHOD AND COMPOSITION ADJUSTED TO THE ISOELECTRIC POINT OF HAIR FOR CONDITIONING OF OXIDATIVELY DYED HAIR

(75) Inventors: Ursula Hehner, Brensbach (DE); Herbert Deutz, Griesheim (DE); Petra Braun, Muenster (DE); Ernst Flemming, Heusenstamm (DE)

(73) Assignee: Wella Aktiengesellschaft, Darmstadt (DE)

( * ) Notice: Subject to any disclaimer, the term of this patent is extended or adjusted under 35 U.S.C. 154(b) by 72 days.

(21) Appl. No.: 10/033,273

(22) Filed: Nov. 13, 2001

(65) Prior Publication Data

US 2002/0122783 A1 Sep. 5, 2002

(30) Foreign Application Priority Data

Nov. 16, 2000 (DE) .......................... 100 56 909

(51) Int. Cl.$^7$ ............................ A61K 7/075; A61K 7/08
(52) U.S. Cl. .................... 424/70.27; 424/400; 424/401; 424/43; 424/47; 424/70.1; 424/70.6; 424/70.11; 424/70.19; 514/880; 514/945
(58) Field of Search ................................ 424/400, 401, 424/43, 47, 70.1, 70.6, 70.11, 70.19, 70.27; 514/880, 945

(56) References Cited

U.S. PATENT DOCUMENTS 5,679,327 A * 10/1997 Darkwa et al. ............ 424/70.4
5,683,685 A * 11/1997 Hirano et al. ............ 424/78.03
6,328,950 B1 * 12/2001 Franzke et al. ............ 424/70.6

FOREIGN PATENT DOCUMENTS

DE 197 35 865 C1 4/1999

OTHER PUBLICATIONS

Chemical and Physical Behavior of Human Hair, Third Edition, Springer Verlag, New York Berlin Heidelberg London Paris Tokyo Hong Kong Barcelona Budapest, pp. 204–206 and 267.

* cited by examiner

Primary Examiner—Thurman K. Page
Assistant Examiner—Charesse Evans
(74) Attorney, Agent, or Firm—Michael J. Striker

(57) ABSTRACT

A method of conditioning and oxidatively dyeing human hair includes applying an oxidative hair dyeing composition to the human hair in order to dye the human hair and, simultaneously or subsequently to the applying of the oxidative hair dyeing composition, applying a particular hair conditioning composition to the hair. This hair conditioning composition has a pH value of from 3.4 to 3.9, which corresponds to an isoelectric point of the human hair, and contains from 0.001 to 2.5% by weight of a cationic polymer, an optional pH buffer and preferably additional conditioning ingredients, such as a cationic surfactant and/or a fatty alcohol.

16 Claims, No Drawings

METHOD AND COMPOSITION ADJUSTED TO THE ISOELECTRIC POINT OF HAIR FOR CONDITIONING OF OXIDATIVELY DYED HAIR

BACKGROUND OF THE INVENTION

The subject matter of the present invention includes a method and composition, which is adjusted to the isoeletric point of hair, for conditioning oxidatively dyed hair as well as a hair treatment product containing this composition.

In hair dyeing one distinguishes between temporary, semi-permanent and permanent hair dyeing. Usually synthetic direct-dyeing or natural dyestuffs, which color the hair when they are absorbed on the hair, are used for temporarily dyeing the hair, i.e. the so-called tinting of hair. Usually oxidation dyes are used for permanent and semi-permanent dyeing, in which the hair dyeing is based on oxidative development of dyestuffs from dye precursors in the interior of hair. The advantage of the direct-dyeing dyestuffs in contrast to the oxidation dyes is that they provide a safer treatment of the hair, since no oxidative damage of the hair occurs. A disadvantage of the direct-dyeing dye compounds is that they are more easily washed out of the hair and thus the dyed hair colors are more difficult to maintain. The direct-dyeing dyestuffs are more rapidly removed by washing from the hair, since they do not dye the cortex of the hair in contrast to oxidative hair dyes, but are only deposited in the scaly layer. Thus a great color change or weakening of the coverage of gray hair takes place after a few hair washings. However oxidative hair dye compounds, especially those that dye hair in the red range, are not completely resistant to more or less strong washing with hair cleansing compositions. Treatment of the hair with an oxidative hair conditioning preparation subsequent to oxidative dyeing of hair is recommended in order to counter oxidative damage to the hair. Conventional hair conditioning preparations are based on fatty alcohols and aqueous emulsions containing cationic surfactant compounds. German Patent Document DE 197 35 865 discloses a composition containing a quaternary ammonium compound, a green tea extract and a cationic polymer for improving the stability or permanence of hair colors obtained by hair dyeing. However oxidative hair dyeing and its stability to washing out with hair cleansing agents are not mentioned and this reference does not disclose that the pH of the composition is critical. The use of this type of product as an after-treatment composition after oxidative hair dyeing of course does cause a certain conditioning of the hair, but the stability of the dyes to washing and/or fading of the dyes after multiple treatments with hair cleaning compositions is not satisfactory.

SUMMARY OF THE INVENTION

It is an object of the present invention to provide a method and composition for conditioning oxidatively dyed hair and at the same time to extend the permanence or stability of the dyed hair colors obtained during the oxidative dyeing of the hair toward washing process.

This object and others, which will be made more apparent hereinafter, are attained by an aqueous hair conditioning preparation adjusted to the isoelectric point of human hair.

During after-treatment of oxidatively dyed hair with a preparation comprising at least one hair-conditioning cationic polymer and adjusted to the isoelectric point of human hair, it was found that the dyed hair, which was treated with the preparation according to the invention, simultaneously was well conditioned and had an improved color stability in contrast to the wash out effect produced with conventional conditioning compositions and subsequent shampooing.

The subject matter of the invention thus includes an aqueous preparation for conditioning of hair dyed with an oxidative dyestuff, which contains at least one polymer with a cationic group and which is adjusted to the isoelectric point of human hair.

Hair comprises proteins. Proteins are characterized, among other things, by an isoionic point and an isoelectric point (C. R. Robbins, Chemical and Physical Behavior of Human Hair, $3^{rd}$ Edition, pp. 204–206,267). The isoionic point is that pH value, at which the number of total positive charges on the protein is equal to the number of total negative charges. The isoionic point of hair is about equal to pH 6.0. The isoelectric point is a surface property of solid proteins and is that pH value at which the number of positive charges on the surface of the protein equals the number of negative charges. The isolectric point of human hair normally is about pH=3.7. The exact value for individual hair can vary slightly from this value. The preparation according to the invention, which has the isoelectric point adjusted to that of human hair, has pH values in a range between 3.4 and 3.9, preferably in a range from 3.5 to 3.8, and especially preferably in a range from 3.6 to 3.8.

Comparative experiments have shown that a hair conditioning composition adjusted to a pH of 3.7 or 3.8 provides improved color stability to washing out than when it has a pH=4.5. Especially good color stability is achieved by the simultaneous use of cationic polymers. Dimethyldiallylammonium chloride/acrylamide copolymer (Polyquaternium-7, MERQUAT® 550L) is a particularly preferred cationic polymer.

Aerosol foam is the preferred application form for the preparation according to the invention. An appropriate aerosol-foam product according to the invention comprises
  (a) a pressure-resistant container,
  (b) a foam head,
  (c) a foam-forming aqueous solution containing at least one polymer, which has a cationic group, adjusted to the isoelectric point of human hair, and
  (d) at least one propellant.

The polymers with cationic groups are preferably contained in an amount of from 0.001 to 2.5 percent by weight, especially preferably from 0.002 to 1.5 percent by weight. Cationic polymers in the sense of the present invention are those polymers, which contain at least one cationic group or cationizable group by protonation. Quaternary amine groups are, for example, cationic groups. Cationizable groups are, for example, primary, secondary or tertiary amine groups. The cationic polymers can be homopolymers or copolymers. The cationic or cationizable groups are contained either in polymer chains or preferably in one or more monomers acting as substituents.

Suitable monomers of the cationic polymers, which have cationizable groups, are unsaturated radically polymerizable compounds, which carry at least one neutralizable or non-neutralizable basic group. The basic groups can especially be primary, secondary or tertiary amine groups, in which the amine nitrogen can also be part of a ring. Monoalkylaminoalkylacrylates, dialkylaminoalkylacrylates, Monoalkylaminoalkylmethacrylates and dialkylaminoalkylmethacrylates are examples of this sort of monomer. The alkyl groups of these monomers are preferably lower alkyl groups, such as those with from one to seven carbon atoms, preferably from one to four carbon atoms.

Suitable monomers, which have quaternary amine groups, include unsaturated, radically polymerizable compounds, which contain at least one quaternary amine group, especially ammonium-substituted vinyl monomers or quaternized derivatives of carboxyvinyl monomers, such as quaternized acrylamides or methacrylamides. For example, acrylamidoalkyltrialkylammonium halogenides or methacrylamidoalkyltrialkylammonium halogenides, trialkylmethacryloxyalkylammonium halogenides, trialkylacryloxyalkylammonium halogenides, dialkyldiallylammonium halogenides or quaternary vinylammonium monomers with cyclic cationic nitrogen-containing groups, such as pyridinium, imidazolium or quaternary pyrrolidones, e.g. alkylvinylimidazolium, alkylvinylpyridinium, or alkylvinyl pyrrolidone salts. The alkyl groups of these monomers are preferably lower alkyl groups, for example $C_1$- to $C_7$-alkyl groups, especially preferably $C_1$- to $C_3$-alkyl groups. Acrylamidopropyltrimethylammonium chloride and methacrylamidopropyltrimethylammonium chloride are preferred.

The cationic polymer can be, if necessary, polymerized with neutral comonomers, which contain neither cationic nor cationizable groups. These neutral comonomers are, for example, acrylamides, methacrylamides, alkylacrylamides and dialkylacrylamides, alkylmethacrylamides and dialkylmethacrylamides, alkylacrylates, alkylmethactrylates, vinylcaprolactones, vinylpyrrolidones, vinyl esters, vinyl alcohols, propylene glycols or ethylene glycols. The alkyl groups of these monomers are preferably lower alkyl groups, for example $C_1$- to $C_7$-alkyl groups, especially preferably $C_1$- to $C_3$-alkyl groups.

Chitosan or a chitosan derivative, which is neutralized with a cosmetically compatible acid, is a suitable cationic polymer. The cosmetically compatible acid can be an organic or inorganic acid, such as formic acid, tartaric acid, malic acid, maleic acid, fumaric acid, pyrrolidone carboxylic acid, citric acid, lactic acid, sulfuric acid, acetic acid, hydrochloric acid, phosphoric acid, or the like. Chitosan derivative compounds can include, for example, quaternary, alkylated or hydroxyalkylated derivative compounds, for example hydroxyethyl chitosan, hydroxypropyl chitosan or hydroxybutyl chitosan.

Preferably the chitosan or chitosan derivative has, preferably, a molecular weight of from 20,000 g/mol to about 5,000,000 g/mol. For example, a low molecular weight chitosan with a molecular weight of from 30,000 to 70,000 g/mol or a high molecular weight chitosan with a molecular weight of from 300,000 to 700,000 g/mol is for example suitable. The preferred deacetylation degree of the chitosan is between 10 and 99%. The neutralization degree for the chitosan or chitosan derivative compound is preferably at least 50%, especially preferably between 70 and 100%, related to the number of free base groups.

Additional suitable cationic polymers include, e.g., polyvinyl pyrrolidone/dimethylaminoethylmethacrylate copolymers, copolymers of polyvinyl pyrrolidone and imidazolimine methochloride, the terpolymer of dimethyldiallylammonium chloride, sodium acrylate and acrylamide, the terpolymer of vinylpyrrolidone, dimethylaminoethylmethacrylate and vinylcaprolactam, quaternized ammonium salts of hydroxyethyl cellulose (INCI name: polyquaternium-10 or polyquaternium-24), cationic guar derivative compounds, vinyl pyrrolidone/methacrylamidopropyltrimethylammonium chloride copolymers or diquaternary polydimethylsiloxanes (INCI name: quaternium-80), stearyldimethylammonium hydroxyethyl cellulose, methacryloylethyl betaine/methacrylate copolymers, polymethacrylamidopropyltrimonium chloride, polyquaternium-2, polyquaternium-6, polyquaternium-7, polyquaternium-18, polyquaternium-22, polyquaternium-27, polyquaternium-39, and polymers with siloxane units, e.g. polyquaternium-41 or polyquaternium-42.

The hair treatment composition according to the invention preferably contains at least one hair conditioning substance selected from the group consisting of fatty alcohols and cationic surfactants. Suitable fatty alcohols include alkanols with 8 to 22 carbon atoms, e.g. myristyl alcohol, cetyl alcohol or stearyl alcohol or their mixtures. The fatty alcohols preferably are contained in the composition in an amount of from 0.5 to 10 percent by weight, especially preferably from 1 to 7.5 percent by weight, and particularly preferably from 1.5 to 5 percent by weight.

The cationic surfactants preferably are contained in the composition according to the invention in an amount of from 0.1 to 10 percent by weight, especially preferably from 0.25 to 7.5 percent by weight and particularly preferably from 0.5 to 5 percent by weight. Suitable cationic surfactants include those surfactants, which contain a quaternary ammonium group. Suitable cationic surfactants can be those of the following formula (I),

$$N^{(+)} R^1 R^2 R^3 R^4 X^{(-)} \tag{I}$$

wherein $R^1$, $R^2$, $R^3$ and $R^4$, independently of each other, is an aliphatic group, aromatic group, alkoxy group, polyoxyalkylene group, alkylamido group, hydroxyalkyl group, aryl group or alkaryl group, each having from one to 22 carbon atoms, with the proviso that at least one of $R^1$, $R^2$, $R^3$ and $R^4$ has at least eight carbon atoms and $X^{(-)}$ represents an anion, e.g. halogen, acetate, phosphate, nitrate or alkylsulfate, preferably a chloride. The aliphatic groups can also contain cross-linking groups or other groups, for example hydroxy groups or additional amino groups, in addition to carbon and hydrogen atoms. Suitable cationic surfactants include the chlorides or bromides of alkyldimethyl-benzylammonium salts, alkyltrimethylammonium salts, e.g. cetyltrimethyl- ammonium chloride or bromide, tetradecyltrimethylammonium chloride or bromide, alkyldimethylhydroxyethylammonium chloride or bromide, dialkyldimethylammonium chloride or bromide, alkylpyridinium salts, e.g. lauryl- or cetylpyridinium chloride or alkylamidoethyltrimethylammonium ether sulfate. Cetyl- and behenyltrimethylammonium chloride and $C_8$- to $C_{20}$-alkybetaine esters salts, e.g. cetylbetaine ester chloride, are especially preferred.

The hair treatment composition according to the invention preferably contains at least one buffer substance or a buffer system, which has a sufficient buffer capacity in a range of about pH 3 to 4, especially at the isoelectric point of human hair. This sort of system is well known to those skilled in the art.

When the hair treatment composition according to the invention is present in the form of an aerosol hair foam product (mousse), it contains at least one known film-forming substance. The composition is foamed with the help of a propellant gas or a chemical propellant, worked into the hair as foam and, after a sufficient acting time for the conditioning effect (at most about 3 to 15 minutes), the composition is rinsed from the hair. The article of manufacture or foam product according to the invention includes an apparatus for foaming the composition in addition to the composition itself. A commercial aerosol foam head can be used for this purpose.

The foam-forming substance is preferably selected from the surfactants, especially non-ionic surfactant compounds with an HLB value of at most 20, preferably from 5 to 18.

The foam-forming surfactant compound is preferably contained in the composition in an amount of from 0.01 to 15, especially preferably from 0.05 to 10, percent by weight. Ethoxylated surfactants having from 1 to 1000 ethylene oxide units, preferably from 1 to 300 ethylene oxide units, especially preferably from 1 to 15 ethylene oxide units.

The foam-forming surfactants preferably include fatty acid glyceride ethoxylates, fatty alcohol ethyoxylates, fatty acid amine ethoxylates, fatty acid alkanol amide ethoxylates and fatty acid ester ethoxylates with from 1 to 50 ethylene oxide (EO) units. For example, ethoxylated lauryl alcohol, tetradecyl alcohol, cetyl alcohol, oleyl alcohol or stearyl alcohol, which can be used alone or in a mixture with each other, and fatty alcohols of ethoxylated lanolin or ethoxylated lanolin are especially preferred. The hair treatment composition of the invention particularly can contain ethoxylated fatty alcohols, which are sold under the trademark DEHYDOL® of Henkel or BRIJ® of ICI Surfactants. Above all, the fatty acid ester ethoxylates can include diglyceride ethoxylates sold under the trademark ARLATONE® G of ICI Surfactants, castor oil ethoxylated with 25 EO units marketed under the trademark CREMOPHOR® EI of BASF, castor oil ethoxylated with 35 EO units and sold under the trademark CREMOPHOR® RH 410, hydrogenated castor oil ethoxylated with 40 EO units marketed under the INCI name PEG-40 hydrogenated castor oil and the raw material sold under the name REWODERM® LI of Witco Surfactants. Preferred non-ionic surfactants include ethoxylated fatty acid sugar esters, especially ethoxylated sorbitan fatty acid esters, which are marketed under the trademarks TWEEN® and ARLACEL® of ICI Surfactants and alkylpolyglycosides marketed under the trademark PLANTAREN® or PLANTACARE® of Henkel or under the trademark ORAMIX® of SEPPIC.

The propellant is contained in the aerosol-foam product according to the invention preferably in an amount of from 1 to 20, especially preferably from 2 to 10, percent by weight. The propellant, for example, can be a lower alkane, such as n-butane, i-butane, propane, butane or also mixtures thereof and dimethyl ether or fluorinated hydrocarbons, such as F152a (1,1-difluoroethane) or F 134 (tetrafluroethane) as well as gaseous propellants, such as $N_2$, $N_2O$ and $CO_2$ as well as mixtures of the foregoing propellants. Propane/butane mixtures are especially preferred.

The foamable composition according to the invention is filled into a pressure-resistant aerosol container, which is provided with a foam-forming head. The container can be made with any of the conventional materials, such as aluminum or tinplate. Foam pressure tubes made from a pressure-resistant plastic material, such as polyethylene terephthalate (PET), are especially preferred.

The subject matter of the invention also includes a method for oxidative dyeing and conditioning hair. In this method the hair is first dyed with a conventional oxidative hair dye composition. Subsequently the hair is treated with an aqueous hair treatment composition, which is adjusted to the isoelectric point of human hair and contains at least one polymer with cationic groups. The hair is preferably rinsed between the hair dyeing step and the subsequent hair treatment step with the hair treatment composition according to the invention. The composition is applied to the moist or wet hair and, after an acting time of preferably from about 3 to 15 minutes during which time it can also be heated, it is rinsed from the hair. Subsequently the hair is dried.

The following examples illustrate the above-described invention in more detail, but the details in these examples should not be considered as limiting the claims appended hereinbelow.

EXAMPLES

Dye Composition A
Kolestron® Perfect Nuance 4/6; Welloxon® 6%
Commercial product of Wella AG
Dye Composition B
Kolestron® Perfect Nuance 6/45; Welloxon® 6%
Commercial product of Wella AG
Conditioning Composition 1 (of the Invention)

| | |
|---|---|
| 2.5 g | cetearyl alcohol |
| 2.0 g | cetyltrimethyl ammonium chloride |
| 0.1 g | MERQUAT® 550 L (Dimethyldiallylammonium chloride/acrylamide copolymer, 8% in water) |
| to 100 g | water, |
| adjusted to pH = 3.8 | |

Treatment Composition 2 (not of the Invention)

| | |
|---|---|
| 2.5 g | cetearyl alcohol |
| 2.0 g | cetyltrimethyl ammonium chloride |
| to 100 g | water, |
| adjusted to pH = 3.8 | |

Treatment Composition 3 (not of the Invention)

| | |
|---|---|
| 2.5 g | cetearyl alcohol |
| 2.0 g | cetyltrimethyl ammonium chloride |
| 0.1 g | MERQUAT® 550 L (Dimethyldiallylammonium chloride/acrylamide copolymer, 8% in water) |
| to 100 g | water, |
| adjusted to pH = 4.5 | |

Comparative Example

Hair Preparation

Samples of bleached natural hairs were each washed with a solution containing a lauryl ether sulfate and oxidatively dyed with the hair dye composition A or B. After the hair dyeing each hair sample was subjected to an after-treatment with conditioning or treatment composition 1, 2 or 3 and dried. Measurements were performed on three samples for each after-treatment composition tested. Each strand was washed 10 times with a hair cleaning composition containing lauryl ether sulfate. As a reference for a quantitative determination of the color in the Lab system a comparison or reference sample was used, which was only dyed and washed once, but it was not subjected to the after-treatment.

Comparative Method

The stability of the color of the dyed hair samples were measured by measuring the color of the samples in the L*a*b* system with the aid of a Minolta spectrophotometer CM-508i (Minolta). Measurements were taken in the root region, the central region and tip region of each hair sample. An average value was determined from the three measured values. The following results are given in the L*a*b* system for describing color. The differences, ΔL, Δa and Δb, of the L*, a* and b* values of the treated hair samples from those of the reference or comparison sample were calculated. The variable, DE, given by the following formula II $$DE = \{\Delta L^2 + \Delta a^2 + \Delta b^2\}^{1/2} \tag{II}$$

is a measure of the change in the color of the hair strands caused by washing them 10 times as described above. The results of the hair samples dyed with dye composition A or B and conditioned with conditioning compositions 1, 2 or 3 are summarized in the following Table I.

TABLE I

COLOR CHANGE PARAMETER, DE, FOR REPEATED WASHINGS OF DYED AND CONDITIONED HAIR SAMPLES

| | | | |
|---|---|---|---|
| Composition 1 & Dye Composition A | DE = 9.86 | Composition 1 & Dye Composition B | DE = 10.15 |
| Composition 2 & Dye Composition A | DE = 15.59 | Composition 2 & Dye Composition B | DE = 12.74 |
| Composition 3 & Dye Composition A | DE = 12.59 | Composition 3 & Dye Composition B | DE = 12.14 |

The conditioning composition 1 of the invention leads to a DE value of 9.86 on dyeing with dye composition A and to a DE value of 10.15 on dyeing with the dye composition B. The composition 2, which is not of the invention because it does not include the cationic polymers, and composition 3 (pH 4.5), also not of the invention because it is not at the isoelectric point, lead to poorer color stability and higher DE values of 15.59 or 12.59 for dyeing with dye composition A and 12.74 or 12.14 for dyeing with dye composition B.

Color differences may be detected visually on the hair samples.

Aerosol Product Example 1

| | |
|---|---|
| 2.5 g | cetearyl alcohol |
| 2.0 g | behenyltrimethyl ammonium chloride |
| 0.1 g | MERQUAT ® 550 L (Dimethyldiallylammonium chloride/acrylamide copolymer, 8% in water) |
| to 100 g | water, |
| adjusted to pH = 3.8 | |

94 percent by weight of the above composition was filled together with 6 percent by weight of a propane/butane propellant gas into a PET foam pressure tube.

Aerosol Product Example 2

| | |
|---|---|
| 2.5 g | cetearyl alcohol |
| 2.0 g | cetylbetaine ester chloride |
| 0.1 g | MERQUAT ®550 L (Dimethyldiallylammonium chloride/acrylamide copolymer, 8% in water) |
| to 100 g | water, |
| adjusted to pH = 3.8 | |

94 percent by weight of the above composition was filled together with 6 percent by weight of a propane/butane propellant gas into a PET foam pressure tube.

The disclosure in German Patent Application P 100 56 909.9-43 of Nov. 16, 2000 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a method and composition adjusted to the isoelectric point of hair for conditioning oxidatively dyed hair, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A hair treatment composition for treating human hair having an isoelectric point, said hair treatment composition having a pH value equal to the isoelectric point of the human hair, said pH value being 3.7±0.1, and said hair treatment composition comprising an aqueous solution of from 0.001 to 2.5% by weight of a polymer having cationic groups.

2. The hair treatment composition as defined in claim 1, wherein said polymer is dimethyldiallylammonium chloride/acrylamide copolymer.

3. The hair treatment composition as defined in claim 1, further comprising at least one member selected from the group consisting of fatty alcohols and cationic surfactants.

4. The hair treatment composition as defined in claim 1, further comprising at least one buffer substance for controlling and maintaining said pH value.

5. An article of manufacture comprising a pressure-resistant aerosol container; a hair treatment composition for treating human hair having an isoelectric point, said hair treatment composition being contained in the aerosol container and a device for generating a foam from said hair treatment composition contained in the aerosol container, said hair treatment composition having a pH value equal to the isoelectric point of the human hair, said pH value being 3.7±0.1, and said hair treatment composition comprising an aqueous solution of from 0.001 to 2.5% by weight of a polymer having cationic groups and from 1 to 20% by weight of at least one propellant.

6. The article of manufacture as defined in claim 5, wherein said polymer is dimethyldiallylammonium chloride/acrylamide copolymer.

7. The article of manufacture as defined in claim 5, wherein said hair treatment composition comprises at least one member selected from the group consisting of fatty alcohols and cationic surfactants.

8. The article of manufacture as defined in claim 5, wherein said hair treatment composition comprises at least one buffer substance for controlling and maintaining said pH value.

9. A method for conditioning and oxidative dyeing of human hair, said method comprising the steps of:
   a) providing a hair conditioning composition having a pH value of from 3.4 to 3.9, said pH value corresponding to an isoelectric point of the human hair, said hair conditioning composition comprising an aqueous solution of from 0.001 to 2.5% by weight of a polymer having cationic groups;
   b) applying an oxidative hair dyeing composition to the human hair in order to dye the human hair; and
   c) simultaneously or subsequently to the applying of the oxidative hair dyeing composition of step a), applying said hair conditioning composition to the hair.

10. The method as defined in claim 9, wherein said polymer is dimethyldiallylammonium chloride/acrylamide copolymer.

11. The method as defined in claim 9, wherein the hair conditioning composition includes at least one member selected from the group consisting of fatty alcohols and cationic surfactants.

12. The method as defined in claim 9, wherein the hair conditioning compositions includes at least one buffer substance for controlling and maintaining said pH value.

13. A hair treatment composition having a pH value from 3.4 to 3.9, said pH value corresponding to an isoelectric point of human hair, and said hair treatment composition consisting essentially of an aqueous Solution of water, from 0.001 to 2.5 percent by weight of a polymer having cationic groups and at least one additive selected from the group consisting of buffers, fatty alcohols and cationic surfactants; and wherein said hair treatment composition contains from 0.5 to 10 percent by weight of at least one of said fatty alcohols, when said at least one of said fatty alcohols is present in said hair treatment composition; and wherein said hair treatment composition contains from 0.1 to 10 percent by weight of at least one of said cationic surfactants, when said at least one of said cationic surfactants is present in said hair treatment composition.

14. The hair treatment composition as defined in claim 13, wherein said polymer is dimethyldiallylammonium chloride/acrylamide copolymer.

15. An article of manufacture comprising a pressure-resistant aerosol container; a hair treatment composition contained in the aerosol container and a device for generating a foam from said hair treatment composition contained in the aerosol container;

wherein said hair treatment composition has a pH value from 3.4 to 3.9 and consists essentially of an aqueous solution of water, from 0.001 to 2.5 percent by weight of a polymer having cationic groups and at least one additive selected from the group consisting of buffers, fatty alcohols and cationic surfactants; and wherein said hair treatment composition contains from 0.5 to 10 percent by weight of at least one of said fatty alcohols, when said at least one of said fatty alcohols is present in said hair treatment composition; and wherein said hair treatment composition contains from 0.1 to 10 percent by weight of at least one of said cationic surfactants, when said at least one of said cationic surfactants is present in said hair treatment composition.

16. The article as defined in claim 15, wherein said polymer is dimethyldiallylammonium chloride/acrylamide copolymer.

* * * * *